United States Patent
Benoit et al.

(10) Patent No.: US 8,348,887 B2
(45) Date of Patent: Jan. 8, 2013

(54) HYDRATING ANHYDROUS GRAFT MATERIALS

(75) Inventors: P. Kevin Benoit, Duxbury, MA (US); Russell Hart, Attleboro, MA (US); James R. Ellsworth, Marshfield, MA (US)

(73) Assignee: Harvest Technologies Corporation, Plymouth, MA (US)

( * ) Notice: Subject to any disclaimer, the term of this patent is extended or adjusted under 35 U.S.C. 154(b) by 356 days.

(21) Appl. No.: 11/793,809

(22) PCT Filed: Dec. 23, 2005

(86) PCT No.: PCT/US2005/046727
§ 371 (c)(1), (2), (4) Date: Jun. 22, 2007

(87) PCT Pub. No.: WO2006/071758
PCT Pub. Date: Jul. 6, 2006

(65) Prior Publication Data
US 2008/0039782 A1 Feb. 14, 2008

Related U.S. Application Data

(60) Provisional application No. 60/638,163, filed on Dec. 23, 2004.

(51) Int. Cl.
*A61M 37/00* (2006.01)
(52) U.S. Cl. .......................... 604/85; 604/82
(58) Field of Classification Search .............. 604/60, 604/82, 85; 606/92, 93; 366/130
See application file for complete search history.

(56) References Cited

U.S. PATENT DOCUMENTS

| | | | | |
|---|---|---|---|---|
| 4,226,236 A | * | 10/1980 | Genese | 604/89 |
| 4,735,616 A | * | 4/1988 | Eibl et al. | 604/191 |
| 5,702,182 A | * | 12/1997 | Alvarado | 366/130 |
| 6,001,259 A | * | 12/1999 | Whitmore | 210/651 |
| 6,045,570 A | * | 4/2000 | Epstein et al. | 606/214 |
| 6,113,257 A | * | 9/2000 | Sharon et al. | 366/130 |
| 6,406,175 B1 | * | 6/2002 | Marino | 366/130 |
| 6,554,803 B1 | | 4/2003 | Ashman | |
| 6,648,133 B1 | | 11/2003 | Blaschke et al. | |
| 6,722,884 B2 | | 4/2004 | Ashman | |
| 6,736,799 B1 | * | 5/2004 | Erbe et al. | 604/181 |
| 7,156,803 B2 | * | 1/2007 | Voellmicke et al. | 600/36 |
| 2001/0034509 A1 | * | 10/2001 | Cragg et al. | 604/369 |
| 2001/0037091 A1 | * | 11/2001 | Wironen et al. | 604/236 |
| 2003/0233067 A1 | * | 12/2003 | McIntosh et al. | 604/82 |
| 2004/0068266 A1 | | 4/2004 | Delmotte | |
| 2004/0122359 A1 | * | 6/2004 | Wenz et al. | 604/82 |
| 2004/0159616 A1 | * | 8/2004 | Cohee et al. | 210/767 |
| 2004/0167617 A1 | * | 8/2004 | Voellmicke et al. | 623/1.23 |
| 2004/0254538 A1 | * | 12/2004 | Murphy et al. | 604/181 |

FOREIGN PATENT DOCUMENTS

WO WO 99/17820 4/1999

* cited by examiner

*Primary Examiner* — Nicholas Lucchesi
*Assistant Examiner* — Gerald Landry, II
(74) *Attorney, Agent, or Firm* — Clark & Brody

(57) ABSTRACT

A container (2) receives anhydrous material to be hydrated and hydrating fluids. The hydrating fluids are introduced into the container through a fluid port (8) by one or more containers having hydrating fluid. The hydrating fluids may be a mixture of fluids provided in any desired proportion. The hydrated material is then ejected from the container.

7 Claims, 2 Drawing Sheets

FIG. 2
FIG. 3
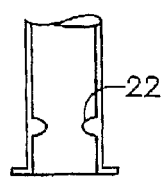
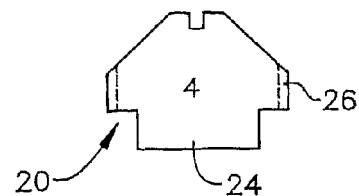

HYDRATING ANHYDROUS GRAFT MATERIALS

CROSS REFERENCE TO RELATED APPLICATIONS

This is a National Phase Entry of PCT/US2005/046727 filed Dec. 23, 2005, which claims the benefit of U.S. Provisional Application Ser. No. 60/638,163 filed on Dec. 23, 2004.

TECHNICAL FIELD

This invention relates to the hydration of anhydrous materials. The invention finds particular utility in the hydration of synthetic or cadaver bone graft materials with a mixture of cell concentrates and thrombin.

BACKGROUND

Surgical procedures and therapies often include the addition of a matrix to facilitate healing. This may be a skin graft or a bone graft. A typical treatment of a bone defect would include debridement, mechanical stabilization, graft application, then closing and caring. There are many sources for graft materials, including cadavers and synthetic materials. It is convenient to manufacture, ship, and store these materials in the anhydrous state. They can be hydrated at the point of care with sterile water, 0.9% NaCl, or biological fluids. Many anhydrous bone graft materials are available both as a contiguous component and granular in structure. A useful hydration method involves hydration with a mixture of platelets, fibrinogen, and thrombin. Using biological fluids, a granular graft material can be hydrated with a clotting fluid, formed into a desired shape, and allowed to clot to improve the handling characteristics in the surgical field.

SUMMARY OF THE INVENTION

In accordance with the invention, a container is provided to receive and contain anhydrous graft material during hydration with a selected hydrating fluid. The container is preferably tubular and provides an opening at one end for placing the anhydrous graft material in the container. The container may take any of various forms, however, and may be made of rigid, semi-rigid or flexible materials. A handle is optionally available for insertion into the container and tamping the graft material against a wall or other surface of the container to insure that the finished graft is free of voids and gaps.

The hydrating fluid is then introduced into the container having the anhydrous material therein by a means for supplying. The fluid may be introduced into the container in any of several ways. For example, the hydrating fluid may be introduced through the opening through which the graft material was inserted. Preferably, the container is provided near the position of the graft material with means for connecting to a source of hydrating fluid. The means for connecting is preferably a fluid port configured to attach easily to containers having the hydrating fluid for transferring the hydrating fluid to the container. Preferably, the fluid port is in the form of a Luer lock for allowing the container to be connected to a variety of known medical products, including syringes and flexible tubes.

The means for supplying, which may be a single source or may be a plurality of sources. If the hydrating fluid is to be obtained from a single source, it can be supplied to the container through the open end through which the graft material was inserted or it may be supplied through the fluid port. In a preferred embodiment, the fluid is supplied through the fluid port by connecting a syringe containing the fluid to the fluid port and injecting the hydrating fluid.

If the hydrating fluid is a mixture of fluids, such as a cell concentrate and thrombin, the means for supplying may comprise two syringes, with each having one of the fluids to be mixed. The two syringes are preferably connected together with a Y-set that combines the fluids into a single stream for introduction to the container. A known such arrangement includes a clip that is attached to the fluid syringe handles whereby the syringes inject the two fluids into the container having the graft to be hydrated at a fixed ratio.

In the preferred embodiment, the container is tubular with one end open and the other end tapering to the fluid port. Means for supporting the material is placed at the end nearest the fluid port for use in ejecting the hydrated graft material. The means for supporting provides support for the material to be hydrated to prevent the break-up of clots during ejection of the material. In this embodiment, hydrating fluid is introduced to the container and injected into the graft material through thru the fluid port. In the preferred embodiment, the means for supporting comprises a piston having channels for passing the hydrating fluid. Alternatively, the means for supporting may be a porous matrix capable of supporting the material, a screen, or the like. Fluid flows evenly about the piston through the channels designed to allow the passage of fluids. If the hydrating fluid includes biologic materials that will form a clot, the tube is allowed to stand until the fluids have clotted the graft.

The hydrated graft is then ejected through the large end of the tube by a means for ejecting. For example, the means for ejecting may comprise a rod, and the material is ejected by pushing the piston with the rod inserted through the other end of the tube, e.g., the fluid port. The means for ejecting may also include structure, such as a sling, that allows the material to be lifted from the container. For example, the material may be ejected by providing an element accessible from the first end of the container to lift the means for supporting and the graft material out of the container. By way of example, a flexible string or cord could be attached to the means for supporting.

The large first end of the tube preferably has an annular ring that forms a stop to retain the means for supporting in the tube. For example, the shape of the piston allows the graft-contacting surface of the piston to extend beyond the end of the container to ensure ejection of the hydrated graft.

When the hydrating fluids are to be a mixture, different fluid syringe diameters of the means for supplying can be used to obtain the desired ratio of fluids delivered to the graft. In the preferred embodiment the clip that attaches to the fluid syringe handles is designed so the syringes will be fully evacuated simultaneously. The volume of a cylinder is the product of pi, the square of the radius, and the length (i.e., $\pi \cdot r^2 \cdot l$). In the preferred embodiment, this system uses a clip on the syringe handles whereby the length is equal for both syringes even when different total volumes are used, which means that one must consider the ratio of the cross sectional areas of the interiors of syringes. So, the hydration fluid delivery ratio is simply the ratio of the syringes' cross-sectional areas ($\pi \cdot r^2$).

Appropriate combinations for standard syringes are:
5:1 for a 20 ml and 3 ml syringe;
3:1 for a 10 ml and 3 ml syringe; and
10:1 for a 10 ml and 1 ml syringe.
Custom syringes with other diameters can be designed to give other ratios.

For two syringes, the hydrating fluid would be whole blood, plasma, platelet rich plasma, platelet poor plasma, platelet concentrate, bone marrow concentrate, or bone marrow aspirate. The second fluid would be bovine or autologous thrombin.

One syringe of fluid can be attached to the tube with a fitting.

Multiple syringes can be attached with a manifold.

The tube may be shapes other than round and may have various diameters. The tube may be of almost any shape, such as a box with a lid.

Graft material can be any anhydrous material, skin, bone, synthetic or cadaver, etc.

A stand (not shown) may also be provided to hold the container upright while clotting.

The invention provides several unique features. For example the invention provides mixing of the thrombin with other fluids as they enter the tube and before distribution to the graft. Different ratios can be obtained by using different diameter syringes for the cell concentrate and the thrombin. The piston is provided with channels adjacent the inside of the tube to distribute the fluid evenly before the fluid is introduced to the graft material. The piston fits the shapes of the tube closely to reduce fluid hold-up volume. The large open end of the tube has a section that is of reduced diameter intended to retain the piston inside the tube. The piston is shaped such that a portion of the graft end of the piston can fit past the reduced diameter of the large open end of the tube. This allows ejection of the graft past the walls of the tube while still retaining the piston in the tube. The length of the rod is such that the handle of the rod becomes incident to the small end of the tube and does not allow the ejection piston to be pushed out of the large end of the tube. The amount of graft material can be varied. The graft material can be tamped inside the tube to reduce voids and gaps in the material. The amount of fluid and the ratio of two or more fluids can be varied.

BRIEF DESCRIPTION OF THE DRAWINGS

FIG. 2 shows the end portion of a preferred container.

FIG. 3 is a side view of a preferred supporting element used with the container of FIG. 2.

DETAILED DESCRIPTION OF THE PREFERRED EMBODIMENT

Figure 1:
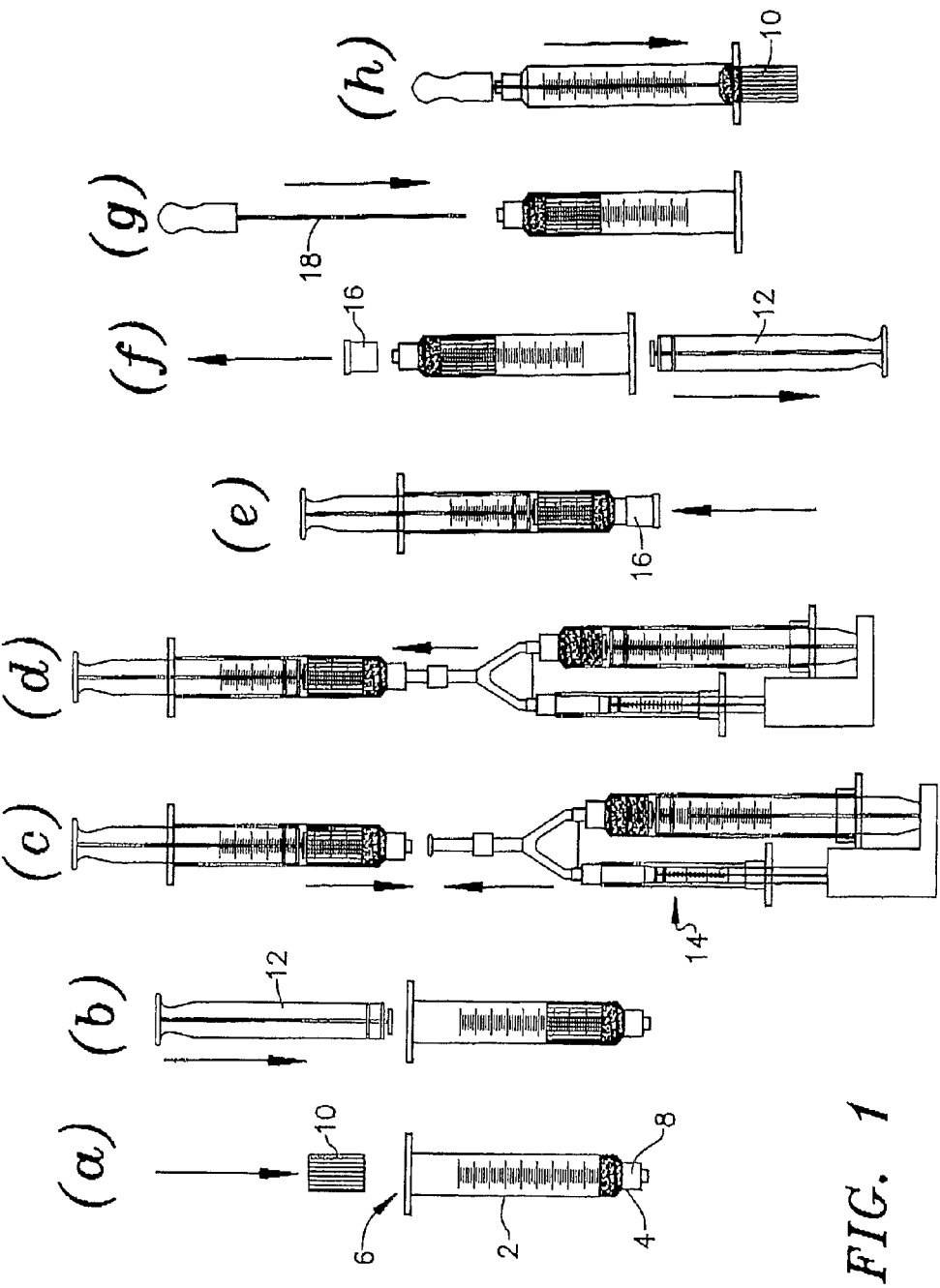
FIGS. 1(*a*) through 1(*h*) show apparatus in accordance with the invention and a process for its use.

With reference to FIG. 1, a preferred embodiment of the invention is illustrated. In FIG. 1*a*, a container 2 in the form of a cylindrical tube similar to a known syringe is provided. The syringe includes a election plug 4, which will be described in detail below. The container has an open upper end 6 and a fluid port 8 at the opposed end. In the step illustrated in FIG. 1*a*, the graft material 10 is placed in the container.

In the step illustrated in FIG. 1*b*, a plunger 12 is inserted through the open end and used to tamp the graft material. The plunger does not seal the cylinder whereby air displaced from the material can escape.

FIG. 1*c* illustrates the connection of a known means for supplying in the form of a dual syringe system 14 that has been supplied with the desired hydration fluid. The system includes two syringes of different volumes and a connector "Y" whereby one syringe, for example, may be supplied with a cellular material and the other with thrombin. The "Y" connector is attached to the fluid port 8, and the plunger of the system 14 advanced to inject fluids into the container 2 as illustrated in FIG. 1*d*.

In FIG. 1*e*, a protective cap 16 is applied to the fluid port after removal of the system 14, and the container is allowed to stand until the fluids clot.

FIG. 1*f* illustrates the first step for ejecting the hydrated graft. In this process, the cap 16 and plunger 12 are removed. An ejection rod 18 is then inserted through the fluid port or other aperture and engaged with the ejection plug 4. Downward pressure forces the plug and graft material downward until the graft is ejected from the container through the end 6 as shown in FIG. 1*h*.

FIGS. 2 and 3 illustrate preferred structures for allowing the plug 4 to extend beyond the end of the container during ejection of the graft. The plug 4 includes a reduced diameter portion forming a shoulder 20. The container, in turn includes a stop 22 formed on the interior surface. The plug may be pushed downward until the stop 22 engages the shoulder 20. At that point, the portion 24 of the plug may be flush with the end of the tube 2, but preferably it is designed such that portion 24 protrudes from the end of the tube to ensure ejection of the graft material.

The plug is further provided with channels 26 to allow free passage of the hydrating fluids during the injection step shown in FIG. 1*d*.

The top of the plug may be configured to mate with the tip of the plunger to allow the plug to be rotated or pushed and pulled during ejection of the plug.

Modifications will be apparent to those of skill in the art.

We claim:

1. Apparatus for facilitating hydration of a material by a fluid comprising a tubular container having an open upper end and a fluid port at an opposite end, said container configured to allow placement of said material into said container through said open upper end and injection of said fluid into said container through said fluid port, an ejection plug in said container configured to support said material on an upper surface thereof when said material is placed in said container through said open upper end, to move in said container from said fluid port to said open upper end, and to allow said fluid injected through said fluid port to flow past said ejection plug, and a plunger configured to be inserted through said fluid port to engage a bottom surface of said ejection plug and move said ejection plug and said material along said container to said upper open end to eject said material from said container.

2. Apparatus according to claim 1 wherein said fluid port is a Luer lock.

3. Apparatus according to claim 1 wherein said plunger comprises an elongate rod.

4. Apparatus according to claim 1 in combination with means for supplying said fluid.

5. A method for hydrating a first material comprising providing the apparatus of claim 1, placing said material in the container through said open upper end, and placing a hydrating fluid in said container adjacent said material through said fluid port.

6. A method according to claim 5 further comprising ejecting said material from said container after said material is hydrated.

7. Apparatus according to claim 1 wherein said ejection plug is shaped such that the ejection plug can be moved to a position where an end of the ejection plug is flush with said upper end.

* * * * *